United States Patent [19]
Przybelski et al.

[11] Patent Number: 6,090,779
[45] Date of Patent: *Jul. 18, 2000

[54] USE OF HEMOGLOBIN TO TREAT SEPTIC SHOCK

[75] Inventors: Robert J. Przybelski, Antioch; Kenneth E. Burhop, Mundelein, both of Ill.

[73] Assignee: Baxter International, Inc., Deerfield, Ill.

[ * ] Notice: This patent is subject to a terminal disclaimer.

[21] Appl. No.: 08/819,878

[22] Filed: Mar. 18, 1997

Related U.S. Application Data

[63] Continuation of application No. 08/471,847, Jun. 7, 1995, Pat. No. 5,614,490, which is a continuation of application No. 08/237,471, May 3, 1994, Pat. No. 5,510,464, which is a continuation of application No. 07/828,429, Jan. 30, 1992, Pat. No. 5,334,706.

[51] Int. Cl.[7] .......................... A61K 38/16; A61K 35/14
[52] U.S. Cl. .................................. 514/6; 514/2; 514/21; 514/832; 514/833; 530/380; 530/385; 424/529; 424/530; 424/533
[58] Field of Search ........................... 514/6, 2, 21, 832, 514/833; 530/380, 385; 424/529, 530, 533

[56] References Cited

U.S. PATENT DOCUMENTS

| | | | |
|---|---|---|---|
| 5,039,520 | 8/1991 | Hunter | 424/83 |
| 5,334,706 | 8/1994 | Przybelski | 530/385 |
| 5,510,464 | 4/1996 | Przybelski | 530/385 |
| 5,614,490 | 3/1997 | Przybelski | 514/6 |

OTHER PUBLICATIONS

Conrad, S.A. "Effect of Red Cell Transfusion on Oxygen Consumption Following Fluid Resuscitation in Septic Shock" Circ. Shock, vol. 31, No. 4, pp. 419–429, Aug., 1990 (1 page Abstract).

Parrat et al. *Applied Cardipuluronary Pthophysiology*, vol. 4, pp. 143–149, 1991.

Kilboun et al, *Proc. Natl. Acad. Sci. USA*, vol. 87, pp. 3629–3632, May 1990.

Kilbourn et al, *Biochemical and Biophysical Research Communication*, vol. 172, No. 3, pp. 1132–1138, Nov. 1990.

Kosaha et al, *Free Radical Biology & Medicine*, vol. 7, pp. 653–658, 1989.

Bagu et al, *European Journal of Pharmacology*, vol. 161, pp. 61–72, 1989.

Martin et al, *The Journal of Pharmacology and Eperimental Therapeutics*, vol. 232, No. 3, pp. 708–716, 1985.

Cross et al, *Infection and Immunity*, vol. 6, No. 7, pp. 2741–2747, Jul. 1993.

Fink et al, *Journal of Surgical Research*, vol. 49, pp. 186–196, Jul. 1990.

Bone, *Annals of Internal Medicine*, vol. 115, No. 6, pp. 457–469, Sep. 1991.

Glauser et al, *The Lancet*, vol. 338, pp. 732–736, Sep. 1991.

*Primary Examiner*—Michael P. Woodward
*Assistant Examiner*—Abdel A. Mohamed
*Attorney, Agent, or Firm*—Senniger, Powers, Leavitt & Roedel

[57] ABSTRACT

Therapeutic treatment of septic shock comprises administering to an animal stroma-free hemoglobin, typically at a dose ranging from the least amount effective to increase perfusion, up to a dosage of about 2500 milligrams kilograms per of body weight.

20 Claims, No Drawings

USE OF HEMOGLOBIN TO TREAT SEPTIC SHOCK

This is a continuation of application Ser. No. 08/471,847, filed Jun. 7, 1995, now U.S. Pat. No. 5,614,490, which is a continuation of application Ser. No. 08/237,471, filed May 3, 1994, now U.S. Pat. No. 5,510,464, which is a continuation of Ser. No. 07/828,429, filed Jan. 30, 1992, now U.S. Pat. No. 5,334,706.

BACKGROUND OF THE INVENTION

The present invention relates to perfusion and specifically to the therapeutic use of hemoglobin in low doses to increase perfusion.

Perfusion is supplying an organ or tissue with oxygen and nutrients via blood or a suitable fluid. Perfusion is essentially the flow of fluid to tissues and organs through arteries and capillaries. Flow may be expressed as the ratio of pressure to resistance. If adequate oxygen and nutrients are not reaching tissues and organs, therapies to improve perfusion may be employed.

Current management of hypotension, and its concurrent reduction in perfusion of tissues and organs, consists of the administration of (i) vasopressors, (ii) positive inotropic agents, and/or (iii) vascular volume expanders depending on the underlying etiology. Hypotension secondary to actual or relative hypovolemia, which also reduces perfusion, initially is managed by administration of crystalloid or colloid solutions and/or blood products.

Therapeutics which increase blood pressure are employed in an attempt to increase perfusion. Vasopressor agents such as epinephrine, phenylephrine, metaraminol and methoxamine cause contraction of the muscles of capillaries and arteries. This increases resistance to the flow of blood and elevates blood pressure. However, these drugs are not optimal for increasing perfusion. They pose a risk of inducing excessive blood pressure; are known to cause arrhythmias; require intraarterial pressure monitoring; and tissue sloughing and necrosis may result if extravasation occurs. Moreover, vasopressor agents may actually decrease the flow of oxygen and nutrients to tissues and organs. If the constriction of the capillaries and arteries increases resistance in proportion to the increase in blood pressure, the net flow, i.e. perfusion, will be unchanged. However, large increases in resistance result in decreased flow. At best a localized increase in perfusion in large vessels occurs while the flow in capillaries is reduced. Indeed, vasopressor agents have been reported to result in decreased perfusion of vital organs. Moreover, because vasopressors increase venous pressure as well as arterial pressure, and, therefore can limit optimal fluid administration, such agents generally are given only after sufficient volume replacement with an appropriate fluid or blood. W. C. Shoemaker, A. W. Fleming, "Resuscitation of the Trauma Patient; Restoration of Hemodynamic Functions Using Clinical Algorithms," Ann. Emerg. Med., 15:1437 (1986). Dopamine hydrochloride is an inotropic agent used in the treatment of shock to increase blood pressure. It suffers from the drawbacks noted above for vasopressor agents. In addition, it has a very small therapeutic window. Because the dose/response is extremely sensitive, dopamine must be carefully titrated, and invasive monitoring (arterial line) is required.

A class of therapeutics known as plasma expanders or volume replacements may be used to increase perfusion where significant blood loss has occurred. In this therapy perfusion is increased by administering volume replacement fluids such as albumin, Ringer's lactate, saline, or dextran solutions. A decrease in blood volume causes a decrease in pressure. By restoring the volume, some pressure, and thus flow can be restored. In addition, these solutions do not carry oxygen or nutrients. So, while flow may be restored, oxygen delivery to the tissues is reduced because oxygen and nutrient content of the blood is diluted. Hemodilution is beneficial in that it reduces the viscosity of the blood, thus reducing resistance and increasing flow. But without the necessary oxygen and nutrients, this therapy is not an optimal treatment for significant blood loss.

Volume replacement with whole blood is currently the most efficacious treatment when there has been significant blood loss. However, this cannot be used in a pre-hospital setting and its use requires a twenty minute wait for matching and typing, assuming a donor blood supply is available. Studies have also shown that the increased viscosity associated with infusion of blood may limit capillary blood flow. K. M. Jan, J. Heldman, and S. Chien, "Coronary Hemodynamics and Oxygen Utilization after Hematocrit Variations in Hemorrhage," Am. J. Physiol., 239:H326 (1980). There is also the risk of viral (hepatitis and/or HIV) or bacterial infection from transfused blood.

Hemoglobin solutions have been under investigation as oxygen carrying plasma expanders or blood substitutes for more than fifty years. While no hemoglobin solution is currently approved for use clinically, they are intended to be used to replace blood lost through hemorrhage. Their effectiveness as oxygen carriers has been demonstrated. However, their potential toxicity has been the focus of much research.

Even small amounts of stroma (cell membrane) in hemoglobin solutions appear to be toxic. R. W. Winslow, "Hemoglobin-based Red Cell Substitutes," The Johns Hopkins University Press, Baltimore (1992). Such toxic effects include renal vasoconstriction and decreased renal flow as well as hypertension and bradycardia. In 1967 Rabiner utilized rigorous purification techniques to develop stroma-free hemoglobin which has prevented some of the toxic effects encountered with prior hemoglobin solutions.

In connection with toxicity studies for hemoglobin solutions researchers noted an elevation in blood pressure as early as 1934. W. R. Amberson, J. Flexner, F. R. Steggerada et al., "On Use of Ringer-Locke Solutions Containing Hemoglobin as a Substitute for Normal Blood in Mammals," J. Cell. Comp. Physiol. 5:359 (1934). Current toxicity studies of hemoglobin solutions continue to note a pressor effect. For example, the replacement of blood with various bovine hemoglobin solutions in rabbits in a 1988 study was characterized by significant hemodynamic instability, with fluctuations of blood pressure and heart rate, and severe tachypinea. Of the various hemoglobin solutions tested in this study, the purest (which comprised cross-linked hemoglobin) showed the least toxicity, but nevertheless "did produce a hypertensive reaction suggestive of a systemic vasoconstrictor effect". M. Feola, J. Simoni, P. C. Canizaro, R. Tran, G. Raschbaum, and F. J. Behal, "Toxicity of Polymerized Hemoglobin Solutions," Surg. Gynecol. Obstet., 166:211 (1988). In 1975 Rabiner reported on the work of a Russian researcher who noted a beneficial effect following administration of 200–400 ml of a 3% hemoglobin solution heavily contaminated with stroma lipid to each of 20 trauma patients, in that there was a stabilization of blood pressure. S. F. Rabiner, "Hemoglobin Solution as a Plasma Expander," Fed. Proc., 34:1454 (1975). In 1949 Amberson et al. reported that the administration of 2300 ml of a 6% to 14% hemoglobin solution (225 grams hemoglobin) restored blood pressure to normal in a patient who had suffered significant blood loss through hemorrhage. W. R. Amberson, J. J. Jennings, and C. M. Rhode, "Clinical Experience with Hemoglobin-Saline Solutions," J. Appl. Physiol., 1:469 (1949).

Although methods of measurement and reporting have been inconsistent, an increase in blood pressure and a fall in heart rate are frequently reported findings associated with administration of a variety of hemoglobin solutions in animals and man. Those researchers noting the pressor effect of solutions include G. A. H. Buttle, A. Kekwick, and A. Schweitzer, "Blood Substitutes in Treatment of Acute Hemorrhage," Lancet, 2:507 (1940). J. H. Miller and R. K. McDonald, "The Effect of Hemoglobin in Renal Function in the Human," J. Clin. Invest., 30:1033 (1951). C. Elia, H. J. Sternberg, A. Greenburg, and G. W. Peskin, "Stroma-free Hemoglobin in the Resuscitation of Hemorrhagic Shock," Surg. Forum, 25:201 (1974). G. S. Moss, R. DeWoskin, A. L. Rosen, H. Levine, and C. K. Palani, "Transport of Oxygen and Carbon Dioxide by Hemoglobin-saline Solution in the Red Cell Free Primate," Surg. Gynecol. Obstet., 142:357 (1976). J. P. Savitsky, J. Doczi, J. Black, and J. D. Arnold, "A Clinical Safety Trial of Stroma-free Hemoglobin," Clin. Pharmacol. Ther., 23:73 (1978). P. E. Keipert and T. M. S. Chang, Pyridoxylated Polyhemoglobin as a Red Cell Substitute for Resuscitation of Lethal Hemorrhagic Shock in Conscious Rats," Biomater. Med. Devices Artif. Organs, 13:1 (1985). F. H. Jesch, W. Peters, J. Hobbhahn, M. Schoenberg, and K. Messmer, "Oxygen-transporting Fluids and Oxygen Delivery with Hemodilution," Crit. Care Med., 10:270 (1982).

Two early animal studies in which hemoglobin solutions were administered following controlled hemorrhage and occlusion of the left coronary artery demonstrated improved myocardial blood flow compared to autologous blood or dextran. G. P. Biro and D. Beresford-Kroeger, "The Effect of Hemodilution with Stroma-free Hemoglobin and Dextran on Collateral Perfusion of Ischemic Myocardium in the Dog," Am. Hrt. J., 99:64 (1980). M. Feola, D. Azar, and L. Wiener, "Improved Oxygenation of Ischemic Myocardium by Hemodilution with Stroma-free Hemoglobin Solution," Chest., 75:369 (1979). Both of these studies were exchange transfusions (1:1 or 2:1) of very large doses of hemoglobin.

Renal complications frequently have been associated with use of high doses of hemoglobin solutions. Oliguria and decreased renal flow have been a common finding, although improved modifications of hemoglobin appear to have somewhat ameliorated this problem. N. I. Birndorf and H. Lopas, "Effect of Red Cell Stroma-free Hemoglobin Solution on Renal Function in Monkeys," J. Appl. Physiol., 29:573 (1970). M. Relihan, R. E. Olsen, and M. S. Litwin, "Clearance Rate and Effect on Renal Function of Stroma-free Hemoglobin Following Renal Ischemia," Ann. Surg., 176:700 (1972). Other reactions such as fever, chills, flushing, nausea, and chest and abdominal pain are often experienced.

In sum, hemoglobin solutions at high doses in high volume administered as oxygen carrying blood substitutes have been reported to increase blood pressure, and this effect has been characterized alternately as toxic or potentially beneficial.

Applicants have now discovered that, surprisingly, low doses of hemoglobin in small volumes may be administered therapeutically to rapidly increase perfusion.

SUMMARY OF THE INVENTION

This invention provides a method to therapeutically increase perfusion in a mammal comprising administering stroma-free hemoglobin at a dose ranging from the least amount effective to increase perfusion, up to a dose of about 2500 mg per kilogram of body weight.

DETAILED DESCRIPTION OF THE INVENTION

This invention is the use of low doses of hemoglobin to increase perfusion in any clinical setting where that positive change is desirable. This includes the administration of hemoglobin to increase blood pressure from abnormally low levels, as in shock of hemorrhagic, cardiogenic or septic origin or to increase blood pressure from normal levels to effect improved perfusion, as in stroke therapy.

The hemoglobin should be "stroma-free" as defined by Rabiner et al. in J. Exp. Med. 126: 1127 to 1142 (1967), and is preferably alpha-alpha crosslinked, prepared by the method described by Przybelski et al. in J. Lab. and Clin. Med. 117: 143–151 (1991). It is preferably human derived, but may be of animal origin or recombinantly produced. It should be in a balanced electrolyte and buffer solution, and preferably is dissolved in one of the plasma expanders such as colloids (plasma, albumin) or crystalloids (saline, glucose, dextran, gelatins, or Lactated Ringer's). The effect of hemoglobin is independent of the diluent used to make up the bulk solution. The hemoglobin should be at a concentration of about 1 to about 20% in solution, depending upon the application. The dose should be from about 30 mg per kg of body weight up to about 2500 mg per kg of body weight. The beneficial effect will plateau after administration of about 125 mg per kg of body weight. Doses greater than this will not enhance the effect, although they will increase the duration of effect.

Conditions in which low dose hemoglobin would be used to rapidly increase perfusion would likely be emergent in nature. Such conditions include shock of hemorrhagic, cardiogenic or septic origin. It would be particularly beneficial in septic shock in which systemic vascular resistance is low causing low blood pressure despite high cardiac output. Under these conditions, hemoglobin would be administered as a bolus of approximately 100 mg (1.0 ml of 10% hemoglobin per kg) followed by volume expansion with a commonly used crystalloid or colloid solution.

Use of hemoglobin to maintain adequate perfusion in a critical care setting would involve slow infusion of a crystalloid/hemoglobin solution 30 mg to deliver a minimum of hemoglobin per kg of body weight, while titrating to effect. The dose administered should give a rise in mean arterial blood pressure equal to or above normal physiologic levels. As used herein the term blood pressure shall mean the mean arterial blood pressure.

This invention has the following advantages over the prior art:

1. It can be administered rapidly (within<1 minute) in small doses (30 mg/kg) as a bolus of approximately 75±25 ml or as a continuous infusion, resulting in immediate restoration of blood pressure and perfusion in an adult. This markedly differs from current dose requirements of crystalloid solutions of 3 times the volume lost, typically necessitating administration of many liters of fluid. Studies in our laboratory also indicate that successful resuscitation of hemorrhagic shock can be achieved with hemoglobin solution of one-sixth the dose of whole blood.

2. The duration of effect on blood pressure of the lowest dose of hemoglobin is about 120 minutes, as compared to the transient (30 minute) rise in blood pressure achieved by administration of Lactated Ringer's, the most commonly used initial resuscitation fluid. This should provide sufficient time to achieve definitive, corrective treatment.

3. It is preferably stroma-free and, therefore, does not require crossmatching or typing. This hastens the time in which definitive treatment enhancing oxygen delivery can be initiated.

4. It can be purified by heat pasteurization and, therefore, free of infective viruses including hepatitis and the human immunodeficiency virus. This is not true of blood products.

5. It is hyperoncotic in nature and, thus, increases intravascular volume. This feature is of particular importance in resuscitation of patients in hemorrhagic shock. Recent reports of the improved results of resuscitation with hyperoncotic saline solutions support the value of this additional feature. P. A. Maningas and R. F. Bellamy, "Hypertonic Sodium Chloride Solutions for the Prehospital Management of Traumatic Hemorrhagic Shock: A Possible Improvement in the Standard of Care?" Ann. Emerg. Med., 15:1411 (1986). C. E. Wade, J. P. Hannon, C. A. Bossone, and M. M. Hunt, "Superiority of Hypertonic Saline/Dextran over Hypertonic Saline During the First 30 Minutes of Resuscitation Following Hemorrhagic Hypotension in Conscious Swine," Resuscitation, 20:49 (1990). D. S. Prough, J. C. Johnson, D. A. Stump et al., "Effects of Hypertonic Saline Versus Lactated Ringer's Solution on Cerebral Oxygen Transport During Resuscitation from Hemorrhagic Shock," J. Neurosurg., 64:627 (1986). J. D. Schmoker, J. Zhuang, and S. R. Shackford, "Hypertonic Fluid Resuscitation Improves Cerebral Oxygen Delivery and Reduces Intracarnial Pressure After Hemorrhagic Shock," J. Trauma, 31:1607 (1991).

6. The magnitude of its effect on blood pressure is non-dose dependent and self-limiting. Both low-doses and high-doses produce a 15–35% increase in mean arterial blood pressure. This important and surprising characteristic of the invention precludes the possibility of an overdose and the development of dangerous hypertension.

7. It has some oxygen carrying ability thereby increasing oxygen delivery to the tissues, albeit less than the oxygen carrying ability of high doses of hemoglobin solutions used as blood substitutes. However, even the small amount of oxygen carrying hemoglobin provided by this invention has a profound beneficial effect when perfusion is concomitantly increased. Increased oxygen delivery is essential to organ viability and is a unique feature of hemoglobin.

8. It has a low viscosity which enhances flow through the microcirculation, thus preserving organ viability and function.

Variations of hemoglobin, including modified hemoglobin, and intramolecular or intermolecular cross-linked species, may be used in accordance with this invention to increase perfusion. The effect of hemoglobin is independent of the diluent used to make up the solution.

Sample guidelines for the clinical administration of hemoglobin solutions in accordance with this invention for three indications are set forth below:

I. To increase perfusion in conditions of hypovolemic shock:
 1. Inject 50 ml (5000 mg) or up to total estimated volume lost of 10% hemoglobin solution (or equivalent) as a bolus into a peripheral IV.
 2. Inject hemoglobin solution within the first or "golden" hour of shock state to minimize duration of decreased perfusion.
 3. Monitor cuff blood pressure every 15 minutes after administration until peak pressure obtained.
 4. Monitor other cardiopulmonary parameters according to standard practice.
 5. Administer other standard therapeutics, as desired or indicated.

II. To increase perfusion in conditions of cardiogenic or septic shock:
 1. Inject 50 ml (5000 mg) IV bolus, or infuse up to 3000 ml (300 g) of 10% hemoglobin solution (or equivalent) at a rate of 1 ml/kg/min to achieve and maintain the desired effect.
 2. Administer hemoglobin as early as possible after the development of a shock state to minimize the duration of decreased perfusion.
 3. Monitor blood pressure (directly or indirectly) every 15 minutes after administration until peak pressure obtained.
 4. Monitor other cardiopulmonary parameters according to standard practice.
 5. Administer other standard therapeutics, as desired or indicated.

III. To increase perfusion in stroke conditions:
 1. Infuse at least 100 ml (10 g) of 10% hemoglobin (or equivalent) intravenously at a rate of 1 ml/kg/min to achieve and maintain the desired effect.
 2. Administer hemoglobin solution as early as possible following the cerebrovascular accident to minimize the duration of decreased cerebral perfusion.
 3. Monitor blood pressure (directly or indirectly) every 15 minutes after administration until peak pressure obtained.
 4. Monitor other cardiopulmonary parameters according to standard practice.
 5. Administer other standard therapeutics as desired or indicated.

Numerous studies have been performed in our laboratory to determine safety and efficacy, characterize the pressor response, define optimal dosage, determine modifying factors, and define agents to counteract the pressor effects of hemoglobin. These have been performed as top-load studies as well as hemorrhage and exchange-transfusion studies.

EXAMPLE ONE

Top-load Studies: Safety and Efficacy/Optimal Dose Study
 Method: Conscious, unrestrained, male, Sprague-Dawley rats (275–350 G) with previously inserted indwelling arterial and venous catheters were assigned to one of the following treatment groups:
 I. 10% hemoglobin solution at doses of 0.625, 1.25, 2.5, 5.0, 10, 20, and 40 ml/kg (equivalent to 62.5, 125, 250, 500, 1000, 2000, and 4000 mg/kg, respectively) (n=6–8)
 II. 8.3% human serum albumin (40 ml/kg)
 III. 10% hemoglobin solution at doses of 10 ml/kg (1000 mg/kg) and 20 ml/kg (2000 mg/kg) intra-arterial or 10% hemoglobin solution at doses of 10 ml/kg (1000 mg/kg) and 20 ml/kg (2000 mg/kg) intravenous.

Blood pressure and heart rate were continuously monitored for 6 hours after infusion.

Results: 10% hemoglobin at doses from 1.25 to 5 ml/kg (125 to 500 mg/kg) produced an abrupt 25–30% increase in mean arterial pressure (MAP) that persisted for 180 minutes. Hemoglobin at 10, 20, and 40 ml/kg (1000, 2000, and 4000 mg/kg), likewise, produced an immediate 25–30% increase in MAP that was sustained for 240 to 300 minutes. Although hemoglobin at 0.625 ml/kg (62.5 mg/kg) produced a 12% increase in MAP, it was not statistically significant compared to baseline. Coincident with the increase in MAP, heart rate (HR) fell in all animals infused with hemoglobin except at the dose of 0.625 ml/kg (62.5 mg/kg). The duration of HR reduction corresponded to the duration of MAP rise. Human serum albumin (HSA) and Ringer's Lactate (RL) did not change MAP or HR significantly compared to baseline. Infusion of hemoglobin 10 ml/kg and 20 ml/kg intraarterially and intravenously resulted in an abrupt increase in MAP and decline in HR that persisted for 240–300 minutes. Statistically, there was no difference between the magnitude and duration of MAP and HR effect between the venous and arterial routes of administration. Cardiac output (CO) determinations were performed in only 2–3 animals receiving hemoglobin at 20 ml/kg or 8.3% HSA (20 ml/kg). Although such few animals preclude statistical analysis, CO values in animals receiving 8.3% HSA rose from a baseline of 30 ml/min to 37 ml/min at the end of infusion. Calculated systemic vascular resistance (SVR) declined from 3200 units at baseline to 2300 units at the end of infusion. In contrast, CO values in animals receiving hemoglobin 20 ml/kg (2000 mg/kg) declined from baseline of 37 ml/min to 34 ml/min at the end of infusion to 26 ml/min by 30 minute post-infusion. Calculated SVR almost doubled from a baseline of 2600 units to 4800 units at the end of infusion, and 4300 units at 30 minutes post-infusion.

Conclusions: Intravenous top-load infusion of up to 40 ml/kg (4000 mg/kg) of 10% hemoglobin solution is well tolerated in conscious rats. Doses of hemoglobin between 1.25 and 40 ml/kg (125 and 4000 mg/kg, respectively) elicit a 30–35% increase in MAP that persists between 180–300 minutes depending on the volume infused. The lowest dose of hemoglobin (0.625 ml/kg or 62.5 mg/kg) produced a (12%) increase in MAP. Concomitant reductions in HR of 30–33% from baseline that persist as long as MAP is elevated suggest a baroreceptor reflex response to the abrupt increase in MAP.

EXAMPLE TWO
Characterization of Pressure Response Study

Methods: Conscious, unrestrained, male, Sprague-Dawley rats with indwelling arterial and venous catheters were assigned randomly to one of four treatment groups:

I. 37° C. 7% hemoglobin 4 ml/kg (280 mg/kg) infused at 0.34 ml/min
II. 37° C. 7% hemoglobin 4 ml/kg (280 mg/kg) as a bolus
III. 4° C. 7% hemoglobin 4 ml/kg (280 mg/kg) infused at 0.34 ml/min
IV. 37° C. 7% hemoglobin 4 ml/kg (280 mg/kg) as a bolus MAP and HR were monitored continuously throughout the infusion and for 120 minutes post-infusion.

Results: Administration of 7% hemoglobin produced a rapid and sustained (120 minutes) rise in MAP in all treatment groups. However, the maximum pressor response was greatest with warm (37°) vs cold (4°) bolus injections of hemoglobin (136±4 mmHg vs 119±6 mmHg). A similar, though less pronounced response occurred with warm (37°) vs cold (4°) infusions of hemoglobin (125±5 mmHg vs 118±5 mmHg, respectively). Varying the rate of administration of cold (4°) solution did not alter the pressor response significantly. However, the pressor response was attenuated with slow infusion (0.34 ml/min) vs bolus administration of warm (37°) hemoglobin (124±5 mmHg vs 134±5 mmHg, respectively). In all cases, HR responded in a reciprocal manner to the changes in MAP. This reflex response was more pronounced (302±11 bpm vs 351±8 bpm) with warm vs cold hemoglobin solution.

The magnitude and duration of the pressor response of 7% hemoglobin (4 ml/kg or 280 mg/kg) is affected by the temperature of the solution with a blunted response observed with administration of cold (4°) versus body temperature (37°) solution. The rate of administration (bolus vs infusion at 0.34 ml/min) did not alter the pressor response significantly, regardless of the solution's temperature.

EXAMPLE THREE
Mechanism of Action Study

Methods: Conscious, male, Sprague-Dawley rats were instrumented with indwelling arterial and venous catheters for continuous monitoring of MAP and HR. The study was divided into two separate sets of experiments: endothelium and nitric oxide/L-NMMA experiments.

Endothelin Study

Animals (1–4 per group) were assigned randomly to receive one of four treatments:

I. Big ET (5 nM/kg), IV bolus
II. Phosphoramidon (5 mg/kg), IV bolus
III. Phosphoramidon (5 mg/kg) pretreatment (30 sec) plus Big ET (5 nM/kg)
IV. Phosphoramidon (5 mg/kg) pretreatment (30 sec) plus 7% hemoglobin (4 ml/kg or 280 mg/kg) IV bolus.

Results: 7% hemoglobin (4 ml/kg or 280 mg/kg) elicited a rapid rise in MAP (105±2 mmHg at baseline vs 133±4 mmHg at 15 minutes post-infusion) which peaked at 15 to 25 minutes and returned to baseline at 120 minutes. Injection of Big ET (5 nM/Kg) elicited a similar, but more dramatic MAP response (98±4 mmHg at baseline vs 149±8 mmHg) which, likewise, peaked at 15 minutes and returned to baseline by 120 minutes. Phosphoramidon, an inhibitor of pro-endothelin conversion to endothelin, given as a top-load injection (5 mg/kg) had no effect on MAP. However, when administered as a 30-sec pre-treatment injection, phosphoramidon (5 mg/kg) attenuated the maximum MAP rise of both Big ET (5 nM/kg) and 7% hemoglobin (4 ml/kg or 280 mg/kg) by approximately 75% and 79%, respectively. HR responded reciprocally with MAP with lowest HR's occurring at maximum MAP. Phosphoramidon, as pre-treatment, also attenuated the magnitude of reduction in HR achieved with both ET and 7% hemoglobin.

Nitric Oxide and L-NMMA Study

Animals (5–7 per group) were assigned randomly to receive one of five treatments:

I. L-NMMA (5 & 10 mg/kg) IV bolus
II. L-arginine (200 mg/kg) IV bolus
III. L-NMMA (5 mg/kg) plus L-arginine (50 & 100 mg/kg) IV bolus
IV. 7% hemoglobin (4 ml/kg or 280 mg/kg) plus L-arginine (200 mg/kg) IV bolus
V. 7% hemoglobin (4 ml/kg or 280 mg/kg) plus Nitroglycerin infusion (titrated at 10–150 mcg/min to effect) begun 15 minutes post-hemoglobin.

Results: L-NMMA injections of 5 and 10 mg/kg increased MAP from 109±3 mmHg to 139±13 mmHg and from 106±2 mmHg to 146±6 mmHg, respectively. This response peaked at 30 minute after injection, and lasted >6 hours. Administration of L-arginine (50 & 100 mg/kg) 30 minute after injection of L-NMMA reduced the L-NMMA's pressor effect significantly (p<0.05). Both the magnitude and duration of this attenuation was greater at the higher dose of L-arginine. Injection of 200 mg/kg of L-arginine in normotensive rats elicited an immediate drop in MAP that quickly rebounded to above baseline levels within 10 minutes. Injection of this same dose (200 mg/kg) of L-arginine 15 minutes after a bolus injection of 7% hemoglobin solution (4 ml/kg or 280 mg/kg) evoked a similar sudden and transient drop in MAP that was followed by an increase in MAP that exceeded that which would be expected from hemoglobin alone. Nitroglycerin (NTG) infusion (10–150 mcg/min) begun at 15 min post 7% hemoglobin injection (4 ml/kg or 280 mg/kg) reduced the pressor effects of hemoglobin, decreasing MAP from a peak of 141±7 mmHg to 113±5 mmHg within minutes. Fifteen minutes after discontinuation of NTG, the MAP remained significantly reduced from control values (115±4 mmHg vs 128±2 mmHg), respectively.

Conclusions: Hemoglobin solution and Big ET (pro-endothelin) have similar pressor effects with respect to MAP peak effect time and duration. However, absolute MAP increase is greater with Big ET than 7% hemoglobin at the doses tested. Phosphoramidon, a metalloproteinase inhibitor, blunts the pressor effect of both Big ET and hemoglobin solution, suggesting that the pressor effect is mediated, at least in part, by ET. Nitroglycerin, a prodrug of nitric oxide (NO), reverses hemoglobin's pressor effects, suggesting that exogenous NO may override hemoglobin's binding of endogenous NO. However, L-arginine, at a dose exceeding that which reversed the pressor effect of L-NMMA, did not reverse the pressor effects of hemoglobin. This suggests that hemoglobin may also interfere with the synthesis of NO. Based on these findings, it is concluded that the pressor effects of hemoglobin are mediated, at least in part, by the release of endothelin (ET), a potent vasoconstrictor, and the inhibition of NO, an endothelin-derived relaxing factor. Thus, hemoglobin's pressor effect is mediated by an autoregulatory system which explains the wide margin of safety of this invention compared to other pressor agents.

EXAMPLE FOUR

Use of Antihypertensive Agents to Control Pressor Response

Methods: Conscious, unrestrained, male, Sprague-Dawley rats (250–350 g) with indwelling arterial and venous catheters were assigned to one of the following five treatment groups, with 6 to 8 animals in each group. MAP and HR were monitored continuously for 120 minutes following infusion.

I. 7% hemoglobin (4 ml/kg or 280 mg/kg) IV bolus

II. 7% hemoglobin (4 ml/kg or 280 mg/kg) IV bolus plus Prazosin (2 mg/kg, IV over 1 min)

III. 7% hemoglobin (4 ml/kg or 280 mg/kg) IV bolus plus Propranolol (70 mcg/kg, IV over 1 min)

IV. 7% hemoglobin (4 ml/kg or 280 mg/kg) IV bolus plus Verapamil (0.25 mg/kg, IV over 1 min, repeated in 10 mins)

V. 7% hemoglobin (4 ml/kg or 280 mg/kg) IV bolus plus Nitroglycerin (IV infusion titrated between 10–150 mcg/min to effect).

Results: 7% hemoglobin infusion elicited an immediate increase in MAP from 105±2 mmHg at baseline to 133±4 mmHg at 15 minutes which was sustained for 120 minutes. HR declined in a reciprocal manner. Injection of Prazosin (2 mg/kg) 15 minutes after injection of hemoglobin, produced an immediate, significant decrease in MAP from a maximum of 134±5 mmHg to 102±11 mmHg with sustained maintenance of MAP near baseline levels for one hour. In response to the effect on MAP, HR was restored to baseline following Prazosin administration, and was sustained throughout the 120 minutes observation period.

Administration of Propranolol (70 mcg/kg) 15 minutes after injection of hemoglobin did not significantly alter its pressor response. An observed brief (3 to 4 minutes) reduction of MAP immediately following Propranolol injection did not achieve statistical significance. Although HR returned near baseline levels, it, likewise did not achieve statistical significance.

Verapamil (0.25 mg/kg) transiently decreased MAP from a peak of 143±7 mmHg to 118±4 mmHg within 2 minutes of injection. However, MAP returned to near baseline within 10 minutes. A second bolus injection of Verapamil produced a similar, transient effect. In response, HR transiently increased toward baseline; however, this did not reach statistical significance.

Nitroglycerin (NTG) infusion over a dose range of 10 to 150 mcg/kg produced an immediate and steady decrease in MAP from a peak of 141±7 mmHg to 113±5 mmHg. Fifteen minutes after discontinuation of NTG, MAP still was significantly reduced compared to baseline (115±4 mmHg vs 138±mmHg, respectively). HR returned to baseline by 15 minutes of NTG infusion and remained at or above baseline for the remainder of the experiment.

Conclusions: The pressor effects of hemoglobin can be controlled readily with clinically relevant doses of at least two commonly used anti-hypertensive agents, Prazosin and Nitroglycerin. The transient effects of Verapamil on MAP raise the question of whether a higher dose and/or continuous infusion might be more effective. Propranolol, at the dose tested, does not effectively control hemoglobin's pressor effect.

EXAMPLE FIVE

Hemorrhage/Exchange Transfusion Studies

Resuscitation Study

Methods: Male Sprague-Dawley rats were anesthetized with an initial dose of 1.2 ml/kg of a 3:7 mixture of xylazine (20 mg/ml) and ketamine (100 mg/ml) and thereafter given 0.6 ml of the same anesthesia solution to maintain anesthesia. Indwelling arterial and venous catheters and Clark-type heated electrodes were placed for continuous monitoring of MAP, HR and transcutaneous oxygen tension for 60 minutes post-treatment. A sham group was not bled except for withdrawal of two 1 ml blood samples, but was monitored the entire period. All other animals were bled a total of 20 ml/kg (approximately one-third total blood volume) at a rate of 1 ml/min. Each rat was assigned randomly to one of six treatment groups: (n=5–15 animals per group).

I. Sham

II. No Resuscitation

III. Autologous Shed Blood (20 ml/kg)

IV. Lactated Ringer's 40 ml/kg

V. 14% Hemoglobin 20 ml/kg (2800 mg/kg)

VI. 14% Hemoglobin 10 ml/kg (1400 mg/kg)

All solutions were infused at a rate of 1.7 ml/min.

Results: Following hemorrhage, the MAP fell to 40% of baseline (to approximately 40 mmHg) in all animals. Within 2 minutes of initiating resuscitation infusion, whole-volume hemoglobin (20 ml/kg) raised MAP to above baseline levels (120 mmHg); half-volume hemoglobin (10 ml/kg) raised MAP to baseline levels (100 mmHg); autologous shed blood raised MAP to approximately 75 mmHg; and Lactated Ringer's raised MAP to 60 mmHg. By four minutes both hemoglobin groups had mean arterial pressures significantly higher than either the Lactated Ringer's or blood groups. By 6 minutes, there were no differences among the MAPs of the blood, full-volume, and half-volume hemoglobin groups, and all remained significantly higher than the no-resuscitation and Lactated Ringer's groups. At 15 minutes post-resuscitation, the MAP of the Lactated Ringers group dropped to the level of the no-resuscitation group. At this same time, the MAP of both the whole-volume and half-volume hemoglobin groups were significantly higher than those of the blood group.

HRs in all groups fell during hemorrhage. Within 2 minutes of resuscitation, HRs in both hemoglobin groups began to rise. By 4 minutes there were no significant differences in HR among the resuscitated groups. However, by 20 minutes, the HRs of the Lactated Ringer's group had fallen to the level of the no-resuscitation group, while that of the hemoglobin and blood groups remained near baseline levels.

All animals that were bled had a drop in transcutaneous oxygen tension ($TCpO_2$) to approximately one-tenth their baseline level. Within 5 minutes of resuscitation infusion, all groups, except the no-resuscitation group, had a rise in $TCpO_2$ to at or near baseline levels. This trend continued in the blood and hemoglobin groups. In contrast, a large, persistent drop in $TCpO_2$ occurred in the Lactated Ringer's group which, by 20 minutes, was not significantly different from the no-resuscitation group.

Measurement of serum lactate levels were not significantly different in all groups prior to hemorrhage. However, post-resuscitation serum lactate levels were significantly increased in the Lactated Ringer's and no-resuscitation groups, whereas the sham, blood, whole-volume, and half-volume hemoglobin groups had no significant change.

Hematocrit levels measured before and 1 hour after hemorrhage showed a significant drop in hematocrit all groups, except for the blood group.

Conclusions: 14% Hemoglobin solution promptly restores MAP, HR, and $TCpO_2$ after non-lethal hemorrhage. The restoration of $TCpO_2$ with hemoglobin solution indicates blood flow peripherally and presumably to other organ systems is enhanced. A clinically significant finding is that half-volume (10 ml/kg) hemoglobin solution is as efficacious in restoring MAP, HR, and $TCpO_2$ as nearly twice that volume of whole blood. The return of MAP to baseline before the hemoglobin solution was completely infused suggests that even a lower dose of the hemoglobin might be effective.

EXAMPLE SIX

Hemorrhage/Dose Optimization Study

Methods: Conscious, unrestrained, male, Sprague-Dawley rats (275–300 g) with indwelling venous and arterial catheters were bled 35 ml/kg manually at 1 ml/min. Twenty minutes after the bleed, the animals were assigned to one of the following treatment groups:
  I. Non-resuscitated control group
  II. Autologous shed blood (35 ml/kg)
  III. Lactated Ringer's (105 ml/kg) at 3 ml/min
  IV. 7% Hemoglobin (17.5 ml/kg=1225 mg/kg or 35 ml/kg=2450 mg/kg) at 1 ml/min
  V. 10% Hemoglobin (17.5 ml/kg=1750 mg/kg or 35 ml/kg=3500 mg/kg) at 1 ml/min
MAP, HR and pulse pressure were monitored for up to 5 hours.

Results: MAP initially fell 31±3 mmHg following hemorrhage and returned to 57% of baseline within 20 minutes. This hypotension was associated with tachycardia. In the non-resuscitated group, MAP remained at 50 to 55 mmHg (from an average baseline of 99.9±4 mmHg) throughout the observation period, and plummeted just prior to death. At 24 hours, 11 out of 15 non-resuscitated animals were dead.

In animals resuscitated with Lactated Ringer's (105 ml/kg), MAP increased to 80% of baseline during the infusion, but fell to 60 to 70% of baseline at completion of infusion and remained at this level throughout the observation period. All animals resuscitated with Lactated Ringer's were alive at 24 hours, although all had significant tachycardia.

Animals resuscitated with Hemoglobin of either 7% or 10%, and at either doses (17.5 ml/kg or 35 ml/kg) as well as animals resuscitated with shed blood had similar hemodynamic responses to resuscitation with an increase in MAP to near or above baseline levels with a concomitant decrease in HR. A slightly greater increase in MAP (120 mmHg vs 110 mmHg) and a slightly lower HR (350 bpm vs 400 bpm) were noted in the animals resuscitated with 10% hemoglobin (both doses) at 60 minutes post-infusion. However, at 120 to 300 minutes post-resuscitation, there were no significant differences between the hemoglobin and blood treated groups. At 24 hours post-resuscitation, 4 of 5 blood treated animals were alive; 8 of 9 animals resuscitated with 10% hemoglobin (17.5 ml/kg or 1750 mg/kg) were alive; 7 of 8 of the 10% hemoglobin (35 ml/kg or 3500 mg/kg) group were alive; 3 of 4 of the 7% hemoglobin (17.5 ml/kg or 1225 mg/kg) group were alive; and 4 of 5 of the 7% hemoglobin (35 ml/kg or 2450 mg/kg) treated animals were alive.

Conclusions: 7% Hemoglobin solution is as efficacious as a 10% hemoglobin solution in restoring MAP and HR following severe hemorrhage. Furthermore, hemoglobin solution at half the volume (17.5 ml/kg or 1225 mg/kg) is as efficacious as blood in restoring cardiovascular function and increasing survival following hemorrhage.

EXAMPLE SEVEN

Hemorrhage Study

Methods: Conscious, York swine (18–23 kg) with indwelling arterial and venous thermodilution catheters were bled 30 ml/kg over a 20 minute period and assigned to one of two treatment groups:
  I. 7% hemoglobin (10 ml/kg; 700 mg/kg) n=6
  II. Autologous shed blood (10 ml/kg) n=6
Following a 2 hour stabilization period, animals received:
  I. Lactated Ringer's (20 ml/kg)
  II. Autologous shed blood (20 ml/kg)
Blood samples for buffered base excess, hematocrit, and arterial blood gases as well as hemodynamic measurements were obtained at baseline, end of hemorrhage, end of first infusion, and end of second infusion.

Results: Following hemorrhage, MAP fell 65% from baseline in Group I animals, and 62% in Group II animals. SVR fell in both groups. Post-hemorrhage HR in Group I decreased 37% from baseline in contrast to a 4% increase in the shed blood group. This contrasting response is explained by the significant difference in baseline HR between Group I (198±10 bpm) and Group II (153±10 bpm).

Following administration of hemoglobin (10 ml/kg; 700 mg/kg), MAP rose by 18% (from a baseline of 106±5 mmHg to 125±9 mmHg). This was accompanied by a 38% decline in HR (from 198±10 mmHg at baseline to 124±5 mmHg), a 10% increase in stroke volume (SV) (from 31 ml/beat at baseline to 34 ml/beat), and an almost doubling of SVR from 18±1.3 to 34±7.1 units.

Following administration of autologous shed blood (10 ml/kg), MAP rose to 96±6 mmHg, but remained 9% below the baseline of 104±8 mmHg. HR remained at control levels and SVR increased from 23.3±2.8 at baseline to 31.4±5.2 units, while SV remained below control values (31 ml/beat vs 25 ml/beat).

At 2 hours post-infusion, animals in Group I (hemoglobin) showed MAPs that remained above baseline, HRs above or close to baseline, continued elevation of SVR, and a decline in SV to 21 ml/beat. At this same time, animals in Group II (autologous blood) experienced further declines in MAP (86±6 mmHg) and HRs (137±7 bpm). SVR in this group declined, but remained above baseline levels at 27.8±4.1 units with essentially no change in SV.

Following the infusion of Lactated Ringer's (20 ml/kg), MAP remained elevated (120±3 mmHg), and HR declined to 160±17 bpm, and SV rose to within 10% of control levels.

Following infusion of 20 ml/kg autologous blood, MAP rose to near, but still below, baseline; HR and SVR declined, and SV increased above baseline levels.

Analysis of blood samples showed a decrease in venous pH in both groups following hemorrhage. This value rebounded slightly (from 7.28 to 7.33) following hemoglobin, but remained depressed at 7.28 following autologous blood. Venous pH returned to normal in both groups following supplemental infusion of Lactated Ringer's or autologous blood.

Buffer base excess (BE) dropped significantly in both groups following hemorrhage, and did not change significantly with infusion of hemoglobin or autologous blood. By 2 hours, BE was returning to baseline in both groups, and increased in both groups following final treatment.

Conclusions: 7% Hemoglobin (10 ml/kg or 700 mg/kg) raises blood pressure more rapidly and to a greater extent than autologous blood, and replenishes buffer base excess equally well.

EXAMPLE EIGHT

Exchange Transfusion Study I

Methods: Conscious, unrestrained rats were bled a total of 60 ml/kg at a rate of 1 ml/min. Infusion of one of the following test solutions was begun after the initial 25 ml/kg bleed while animals were bled an additional 35 ml/kg. (n=8 animals in each group).

I. 7% Hemoglobin (10 ml/kg=700 mg/kg) followed by Lactated Ringer's (50 ml/kg) to total volume lost (60 ml/kg)

II. 7% Hemoglobin (20 ml/kg=1400 mg/kg) followed by Lactated Ringer's (120 ml/kg)

III. Lactated Ringer's (180 ml/kg)

All infusions were given at a rate of 1 ml/min until completion of bleeding, and then increased to 3 ml/min. MAP and HR were monitored continuously for 2 hours. Venous blood samples were analyzed for blood gases, electrolytes, and hematocrit at baseline, end-of-resuscitation, and 1 hour post-resuscitation.

Results: Following the initial bleed of 25 ml/kg, MAP fell to approximately 30 mmHg. By mid-transfusion (end-of-bleed), MAP was significantly higher and near baseline level only in the group receiving the higher dose (20 ml/kg or 1400 mg/kg) of 7% hemoglobin. This response was sustained for the entire observation period (120 minutes). MAP in animals receiving the lower dose (10 ml/kg or 700 mg/kg) of 7% hemoglobin rose to approximately 70 to 80 mmHg at the end of infusion, and was sustained for 120 minutes. In the Lactated Ringer's group, MAP was restored to only 60 mmHg (from a baseline of 98 mmHg) at the end of the infusion, and thereafter continued to decline with all animals dead within 60 to 90 minutes post-infusion. Animals in both hemoglobin groups survived longer: 90±9 minutes in the lower dose hemoglobin group and 277±50 minutes in the higher dose hemoglobin group.

Blood gas data showed lower $HCO_3$, $pCO_2$, and pH levels (metabolic acidosis) in the Lactated Ringer's group compared to the hemoglobin treated groups. Serum $K^+$ levels were significantly increased from baseline in the Lactated Ringer's groups, but were oily significantly increased at 1 hour post-resuscitation in both hemoglobin groups.

Conclusions: 7% Hemoglobin solution at a dose of 20 ml/kg (1400 mg/kg) followed by 3:1 Lactated Ringer's is superior to lower dose 7% Hemoglobin (10 ml/kg or 700 mg/kg) followed by 1:1 Lactated Ringer's, and both hemoglobin doses were superior to 3:1 Lactated Ringer's alone. This study demonstrates that 20 ml/kg or 1400 mg/kg of 7% Hemoglobin is sufficient for resuscitation following hemorrhage for up to 3 to 4 hours if adequate crystalloid is infused following hemoglobin administration.

This period of adequate tissue oxygenation may provide the necessary and critical time before definitive treatment is available.

EXAMPLE NINE

Exchange-Transfusion Study II

Methods: Conscious, unrestrained rats were bled a total of 70 ml/kg (approximately total blood volume) at a rate of 1 ml/min. Infusion of one of the following test solutions was begun after an initial bleed of 35 ml/kg, while the animals continued to be bled an additional 35 ml/kg. (n=6–8 animals per group)

I. 7% Hemoglobin (20 ml/kg=1400 mg/kg) followed by Lactated Ringer's (50 ml/kg) to total volume lost of 70 ml/kg II. Lactated Ringer's (210 ml/kg) to total 3 times the volume lost III. 5% Human Serum Albumin (HSA) 70 ml/kg All infusions were given at a rate of 1 ml/min until completion of the bleed, and then increased to 3 ml/min.

Venous blood samples were analyzed for blood gases, electrolytes and hematocrit at baseline, end-of-resuscitation, and 1 hour post-resuscitation.

Results: MAP fell uniformly to approximately 35 to 40 mmHg at the end of the initial 35 ml/kg bleed. Animals transfused with Lactated Ringer's had a transient increase in MAP (to 50 mmHg) that fell precipitously even before the completion of infusion. HR also remained low during this treatment but increased significantly by 20 minutes post-resuscitation. By 60 minutes, the one remaining animal in this group had tachycardia with a HR>450 bpm in response to severe hypotension. Animals transfused with HSA had MAPs restored to approximately 60 mmHg. These animals had considerable tachycardia (450–500 bpm) throughout the observation period. By 60 minutes, one animal in the HSA group was alive. Animals resuscitated with 7% hemoglobin had a restoration of MAP to baseline during and up to 30 minutes post-resuscitation. However, by 60 minutes, only 2 of the hemoglobin treated animals were alive, and their MAPs were decreasing. HR was rapidly restored to or above baseline for at least 30 minutes post-resuscitation. By 60 minutes, HR fell as circulatory function collapsed. Survival time was not significantly different between the Lactated Ringer's and HSA treated animals, but was significantly better in the hemoglobin-transfused animals.

All resuscitated animals were extremely acidotic by the end of resuscitation and at 1 hour post-resuscitation with significant drops in $HCO_3$, pH and $pCO_2$. Serum $K^+$ levels were significantly elevated reflecting significant cellular damage from ischemia and hypoxia.

Conclusions: In this more severe transfusion-exchange model, 7% hemoglobin was superior to 3:1 Lactated Ringers, or isovolume 5% HSA. However, in this model, hemoglobin solution was able to restore and maintain MAP for only 30 minutes. Although blood gases and chemistries were considerably better in the hemoglobin-treated animals, by 1 hour post-resuscitation animals were decompensating and became as metabolically acidotic as animals in the other two groups. It is possible that increasing the volume of Lactated Ringer's (3:1 vs 1:1) following hemoglobin infusion may improve results.

EXAMPLE TEN

Tissue Flow Study

Methods: Conscious York swine with indwelling venous and right ventricular catheters were bled 30 ml/kg over 30 minutes. Following hemorrhage, venous blood samples were analyzed for base excess; when BE reached −5 to −10, infusion of 7% hemoglobin 5 ml/kg (350 mg/kg) was infused at a rate of 1 ml/kg/min. Animals were monitored for 1 hour post-infusion at which time they were sacrificed for assessment of organ flow.

Results: MAP fell from a mean of 100 mmHg to 40 mmHg following hemorrhage and promptly returned to baseline following infusion of a very small volume of hemoglobin.

Flow to all organs except the adrenals and the liver, declined following hemorrhage. Following infusion of 7% hemoglobin, tissue flow increased to all organ systems except the lung and the liver. Importantly, tissue flow had increased to above baseline levels to the heart and the brain. At 1 hour post-resuscitation, flow to all organs was increased except to parts of the splanchnic system.

Conclusions: Seven percent hemoglobin solution effectively restored MAP following acute hemorrhage. This is associated with an increase in perfusion to vital organ systems, and all other organs with the exception of the lung and the liver. This was achieved with doses as low as 5 ml/kg (350 mg/kg) or one sixth of the blood volume lost.

EXAMPLE ELEVEN

Cerebral Perfusion Study

Methods: Male, spontaneously hypertensive, anesthetized, and mechanically ventilated rats (350–400 g) with indwelling venous and arterial catheters were assigned randomly to one of the following treatment groups: (n=9 animals per group).

I. Hematocrit 44%: blood volume increased with 8 ml donor blood
II. Hematocrit 37%: blood volume & hematocrit manipulated with 8 ml (560 mg) 7% hemoglobin
III. Hematocrit 30%: blood volume and hematocrit manipulated by 5 ml (350 mg) exchange transfusion of 7% hemoglobin plus an additional 8 ml (560 mg) 7% hemoglobin
IV. Hematocrit 23%: blood volume and hematocrit manipulated by 10 ml (700 mg) exchange transfusion of 7% hemoglobin plus an additional 8 ml (560 mg) 7% hemoglobin
V. Hematocrit 16%: blood volume and hematocrit manipulated by 15 ml (1050 mg) exchange transfusion of 7% hemoglobin plus an additional 8 ml (560 mg) 7% hemoglobin
VI. Hematocrit 9%: blood volume and hematocrit manipulated by 20 ml (1400 mg) exchange transfusion plus an additional 8 ml (560 mg) 7% hemoglobin Maintenance fluids of 0.9 NaCl were infused at 4 ml/kg/hr and target hematocrits and blood volumes maintained for 30 minutes. Via a craniectomy, the middle cerebral artery (MCA) was occluded. After 10 minutes of occlusion, 100 uCi-kg of C-iodoantipyrine was given. Brains were then removed, sectioned, and analyzed to define areas with cerebral blood flow (CBF) 0–10 ml/100 g/minute and 11–20 ml/100 g/min.

Results: There was no difference between the hematocrit 44% and hematocrit 37% groups in areas of 0–10 and 11–20 ml/100 g/minute CBF. In the other 4 groups, the areas of both of these low CBF's were less as hematocrit decreased, with the smallest area of ischemia occurring in the hematocrit 9% group (the group that received the largest dose of hemoglobin). Measurements of CBF in the hemisphere contralateral to the occluded MCA revealed a progressive increase in CBF as hematocrit decreased (from 125.6±18.8 ml with hematocrit 44% to 180.8±14.4 ml with hematocrit 9%).

Conclusions: Hypervolemic hemodilution with 7% hemoglobin effects a dose-related decrease in ischemia following 10 minutes of MCA occlusion in rats. This occurs in association with increased perfusion (CBF) related to increased doses of hemoglobin.

While the foregoing embodiments are intended to illustrate a novel therapeutic method to increase perfusion, they are not intended nor should they be construed as limitations on the invention. As one skilled in the art would understand, many variations and modifications of these embodiments may be made which fall within the spirit and scope of this invention.

What is claimed is:

1. A method for increasing the mean arterial pressure in a patient suffering from septic shock comprising administering a therapeutically effective amount of intermolecularly- or intramolecularly-crosslinked stroma-free hemoglobin to the patient.

2. The method of claim 1 wherein the hemoglobin is of animal origin.

3. The method of claim 1 wherein the hemoglobin is human derived.

4. The method of claim 1 wherein the hemoglobin is recombinantly produced.

5. The method of claim 1 wherein the hemoglobin is administered to the patient during emergent care.

6. The method of claim 1 wherein from about 30 to about 2,500 milligrams of hemoglobin per kilogram of body weight are administered to the patient.

7. The method of claim 1 wherein from about 30 to about 1,000 milligrams of hemoglobin per kilogram of body weight are administered to the patient.

8. The method of claim 1 wherein from about 30 to about 500 milligrams of hemoglobin per kilogram of body weight are administered to the patient.

9. A method for increasing perfusion in a patient suffering from septic shock comprising administering a perfusion-increasing effective amount of intermolecularly- or intramolecularly-crosslinked stroma-free hemoglobin to the patient.

10. The method of claim 9 wherein about 100 milligrams of hemoglobin per kilogram of body weight are administered to the patient.

11. The method of claim 9 wherein the hemoglobin is of animal origin.

12. The method of claim 9 wherein the hemoglobin is human derived.

13. The method of claim 9 wherein the hemoglobin is recombinantly produced.

14. The method of claim 9 wherein the hemoglobin is administered to the patient during emergent care.

15. The method of claim 9 wherein from about 30 to about 4,000 milligrams of hemoglobin per kilogram of body weight are administered to the patient.

16. A method for reducing hypotension secondary to septic shock in a patient suffering from septic shock comprising administering a blood pressure-increasing effective amount of intermolecularly- or intramolecularly-crosslinked stroma-free hemoglobin to the patient.

17. A method for reducing hypotension secondary to septic shock in a patient suffering from septic shock comprising administering from about 30 to about 4,000 milligrams of intermolecularly- or intramolecularly-crosslinked stroma-free hemoglobin per kilogram of body weight to the patient.

18. The method of claim 17 wherein from about 30 to about 2,500 milligrams of hemoglobin per kilogram of body weight are administered to the patient.

19. The method of claim 17 wherein from about 30 to about 1,000 milligrams of hemoglobin per kilogram of body weight are administered to the patient.

20. The method of claim 17 wherein from about 30 to about 500 milligrams of hemoglobin per kilogram of body weight are administered to the patient.

* * * * *